(12) United States Patent
Prini

(10) Patent No.: US 8,790,685 B2
(45) Date of Patent: Jul. 29, 2014

(54) BIOADHESIVE GEL BASED ON HYDROXYETHYLCELLULOSE

(75) Inventor: Massimo Prini, Milan (IT)

(73) Assignee: Mipharm S.p.A., Milan (IT)

( * ) Notice: Subject to any disclaimer, the term of this patent is extended or adjusted under 35 U.S.C. 154(b) by 4 days.

(21) Appl. No.: 13/293,484

(22) Filed: Nov. 10, 2011

(65) Prior Publication Data

US 2012/0083515 A1 Apr. 5, 2012

Related U.S. Application Data

(63) Continuation of application No. 10/567,890, filed as application No. PCT/EP2004/008577 on Jul. 30, 2004, now abandoned.

(30) Foreign Application Priority Data

Aug. 8, 2003 (IT) .............................. MI2003A1640

(51) Int. Cl.
A61K 47/38 (2006.01)

(52) U.S. Cl.
USPC .......................................... 424/433; 514/399

(58) Field of Classification Search
CPC ..................................................... A61K 9/0036
USPC .......................................... 514/399; 424/433
See application file for complete search history.

(56) References Cited

U.S. PATENT DOCUMENTS

| | | | | |
|---|---|---|---|---|
| 6,159,491 | A | 12/2000 | Durrani | 424/430 |
| 6,416,779 | B1 * | 7/2002 | D'Augustine et al. | 424/430 |
| 7,214,381 | B2 * | 5/2007 | Carrara et al. | 424/400 |
| 2002/0012674 | A1 | 1/2002 | Saettone et al. | 424/400 |
| 2003/0039704 | A1 | 2/2003 | Arkin et al. | |
| 2003/0091642 | A1 | 5/2003 | Auzerie | 424/486 |
| 2004/0102429 | A1 * | 5/2004 | Modak et al. | 514/184 |

FOREIGN PATENT DOCUMENTS

| | | |
|---|---|---|
| WO | WO 96/10989 | 4/1996 |
| WO | WO 00/15192 | 3/2000 |
| WO | WO 00/47144 | 8/2000 |
| WO | WO 01/28515 A1 | 4/2001 |
| WO | WO 01/43720 A1 | 6/2001 |
| WO | WO 02/03896 A1 | 1/2002 |
| WO | WO 03/094920 A1 | 11/2003 |

OTHER PUBLICATIONS

Jones David S et al: Textural viscoelastic and mucoadhesive properties of pharmaceutical gels composed of cellulose polymers: International Journal of Pharmaceutics (Amsterdam) vol. 3 151, No. 2, 1997, pp. 223-233, XP002311525.
Carlan S. J et al: "Extemporaneous preparation of misoprostol gel for cervical ripening: A randomized trial" Obstetrics and Gynecology, vol. 90, No. 6, Dec. 1997, pp. 911-915, XP002311526.
Syed Tanweer A et al: "Management of intravaginal warts in women with 5-fluorouracil (1%) in vaginal hydrophilic gel: A placebo-controlled double-blind study" International Journal of STD and AIDS, vol. 11, No. 6, Jun. 2000 92000-06 0, pp. 371-374, XP009041891.
Birnie Christine R et al: "Antimicrobial and diffusional correlation of N-alkyl betaines and N-alkyl-N, N-dimthylamine oxides from semi-solids" Journal of Pharmaceutical Sciences, vol. 90, No. 9, Sep. 2001, pp. 1386-1394, XP002311527.
Ballagh S A et al: "Safety of single daily use for one week of C31G HEC gel in women." Contraception, vol. 66, No. 5 Nov. 2002, pp. 369-375, XP002311528.
International Search Report PCT/EP2004/008577 dated Dec. 20, 2004.
Remington's Pharmaceutical Sciences, 17$^{th}$ ed. (1985), A.R. Gennaro (ed.), pp. 290-293.
Di Shayne Cox Gad, Pharmaceutical Manufacturing Handbook: Production and Processes, vol. 10, pp. 288 and 291, 2008 (Google Library).
Gavin P. Andrews, Thomas P. Laverty, David S. Jones, "Mucoadhesive polymeric platforms for controlled drug delivery," European Journal of Phamaceutics and Biopharmaceutics 71 (2009) 505-518.
John D. Smart, "The basics and underlying mechanisms of mucoadhesion," School of Pharmacy and Biomolecular Sciences, University of Brighton, Lewes Road, Brighton BN2 4GJ, UK, Advanced Drug Delivery Reviews, vol. 57, pp. 1556-1568, 2005.
Edsman Katarina; Hägerström Helene, Pharmaceutical applications of mucoadhesion for the non-oral routes, available online at http://cat.inist.fr/?Modele=afficheN&cpsidt=16419936, Journal of Pharmacy and Pharmacology, vol. 57, No. 1, Abstract, 2005.
Bioadhesion—Encyclopedia of Biomaterials and Biomedical Engineering, Gary L. Bowlin; Gary Wnek, 2004, available online at http://www.informaworld.com/smpp/content~db=all~content=a713553984.
Mucoadhesive Polymers—A Review | Pharmainfo.net, 2006, available online at http://www.pharmainfo.net/reviews/mucoadhesive-polymers-review.
International Preliminary Report on Patentability dated Nov. 22, 2005 in corresponding International Application No. PCT/EP2004/008577.
Written Opinion of the International Searching Authoritty dated Dec. 20, 2004 in corresponding International Application No. PCT/EP2004/008577.

* cited by examiner

*Primary Examiner* — Jake Vu
(74) *Attorney, Agent, or Firm* — Silvia Salvadori, P.C.

(57) ABSTRACT

Disclosed are compositions in the form of a bioadhesive gel that adheres to the mucous membranes, in particular the vaginal mucosa, for the application of active ingredients and/or principles, comprising hydroxyethylcellulose as the only gelling agent.

5 Claims, 4 Drawing Sheets

BIOADHESIVE GEL BASED ON HYDROXYETHYLCELLULOSE

CROSS-REFERENCE TO RELATED APPLICATIONS

The present application is a continuation of prior U.S. patent application Ser. No. 10/567,890, filed Sep. 15, 2006, entitled "BIOADHESIVE GEL BASED ON HYDROXYETHYLCELLULOSE," which is a 35 U.S.C. §371 National Phase conversion of PCT/EP2004/008577, filed Jul. 30, 2004, which claims priority of Italian Application No. MI2003A001640, filed Aug. 8, 2003, the entire disclosures of which are incorporated herein by reference. The PCT International Application was published in the English language.

TECHNICAL FIELD

This invention relates to compositions in the form of a bioadhesive gel that adheres to the mucous membranes, in particular the vaginal mucosa, for the application of active ingredients and/or principles.

BACKGROUND OF THE INVENTION

Bioadhesion is the property whereby some hydrogels adhere to biological tissues, in particular to mucous-coated epithelia such as the gastric, buccal, vaginal and rectal mucosae.

This property has been exploited to develop drug delivery systems, especially in order to increase the time over which drugs remain in contact with certain sites or areas of therapeutic interest, giving rise to systemic effects (thus increasing transmucosal absorption) or local effects.

The most commonly used polymers that are capable of forming hydrogels and imparting bio- and/or muco-adhesion are acrylic or methacrylic acid polymers, possibly cross-linked, and chitosan, or its derivatives.

In particular, for drugs designed for gynaecological use, a bioadhesive gel able to ensure prolonged contact between the active ingredient and the vaginal mucosa, and gradual release of that ingredient over time, provides the ideal solution in terms of efficacy and compliance by patients.

Bioadhesive vaginal gels have consequently been disclosed, for example, in U.S. Pat. No. 6,159,491, US 2002012674, US 2003091642, WO 200047144, WO 200203896, WO 200143720 and WO 9610989. In all these cases, an acrylic acid polymer (Carbomer or polycarbophil) is used as viscosity-controlling or bioadhesive agent.

WO 200015192 describes mucoadhesive formulations in which chitosan is used instead of the acrylic acid polymer.

However, the problem of obtaining a bioadhesive formulation that presents the following advantages and properties:
release of drug for up to approximately 24 hours;
absence of gelling/bioadhesive agents, characterised by the presence of acid groups, which are therefore sensitive to the ionic strength of the medium, and sometimes need to be neutralised with bases;
the possibility of carrying drugs with different chemico-physical properties, in particular water-soluble drugs and lipophilic drugs which are substantially insoluble in water;
reduction of the time and cost of the treatment
remains substantially unsolved.

SUMMARY OF THE INVENTION

It has now been found that said objectives can be achieved by bioadhesive gel formulations that adhere to the mucous membranes, in particular the vaginal mucosa, comprising hydroxyethylcellulose as the only bioadhesive polymer. This gelling excipient has no acid groups and is therefore not dependent on the ionic strength of the medium; it also has a matrix effect which allows particularly slow, gradual release of the active ingredient, for up to 24 hours.

DETAILED DESCRIPTION

This invention therefore relates to compositions in the form of an aqueous gel for the intravaginal delivery of active ingredients, comprising hydroxyethylcellulose as the only gelling and bioadhesive agent.

The compositions of the invention may also contain glycerol, diethylene glycol monoethyl ether, surfactants, preservatives, acidifiers and other excipients in common use for the form of delivery considered herein.

The compositions of the invention will preferably contain 1 to 5% by weight of hydroxyethylcellulose, 25 to 90% by weight of water, 5 to 25% by weight of glycerol, 5 to 50% by weight of diethylene glycol monoethyl ether, 0.01 to 10% by weight of surfactants, 0.05 to 1% by weight of preservatives, and 0.01 to 1% by weight of acidifiers.

Preferably, the hydroxyethylcellulose content is higher than 2% and less than 4%.

Hydroxyethylcellulose is commercially available from many sources: it is preferred an hydroxyethylcellulose having a degree of substitution of about 1.5 (corresponding to 3 hydroxyethyl groups every two saccharide units) and a molecular weight estimated from intrinsic viscosity measurements ranging from 1.0 to $1.3 \times 10^6$. Hydroxyethylcellulose having said characteristic is available under the trade-mark Natrosol 250 HX by Hercules Inc. UK.

The percentage of active ingredient will obviously depend on the characteristics of the selected drug, and may vary within a wide range, for example from 0.01 to 10% by weight.

Active ingredients which can be advantageously formulated according to the invention include antifungals, antiseptics and antimicrobials, antibiotics, analgesics, local anaesthetics, antihistamines, anti-inflammatory agents, contraceptives, hormones, and combinations thereof.

Examples of these active ingredients include, in particular, econazole, miconazole, fluconazole, ciclopiroxolamine, nifuratel, nystatin, chlorhexidine, ibuprofen, ketoprofen, naproxen, benzydamine, benzalkonium chloride or other quaternary ammonium antiseptics, nonoxynol-9 and all other active ingredients of interest for gynaecological applications.

EXAMPLES

The following examples are provided only for the purpose of illustrating the invention and do not limit the invention in any manner.

Example 1

| Composition | Percentage |
| --- | --- |
| Purified water | 81.9% |
| Glycerol | 12.9% |
| Chlorhexidine digluconate, 20% solution w/v | 2.7% |
| Hydroxyethylcellulose (Natrosol 250 HX) | 2.5% |

Example 2

Ibuprofen Vaginal Gel

| Composition | Percentage |
|---|---|
| Ibuprofen | 0.100% |
| Benzalkonium chloride | 0.150% |
| Polyoxyethyen-20-monocetyl ether (Brij 58) | 0.500% |
| Hydroxyethylcellulose (Natrosol 250 HX) | 2.500% |
| Diethylene glycol monoethyl ester (Transcutol P) | 10.000% |
| Purified water | 86.750% |

Example 3

Econazole Nitrate Vaginal Gel

| Composition | Percentage |
|---|---|
| Econazole nitrate | 1.000% |
| Benzalkonium chloride | 0.150% |
| Hydroxyethylcellulose (Natrosol 250 HX) | 2.500% |
| Polysorbate 80 (Tween 80) | 4.000% |
| Glycerol | 10.000% |
| Diethylene glycol monoethyl ester (Transcutol P) | 40.000% |
| Purified water | 42.350% |

Example 4

Study of Bioadhesion of Vaginal Gels

Bioadhesion was measured in vitro using a suitably modified Lloyd dynamometer. The measurement substrate (rabbit gastric mucosa or polypropylene) was fixed with an adhesive to the upper support, which in turn was connected to the mobile crossbar, and 200 mg of the test formulation were placed on the lower support so as to cover the surface evenly. After effecting close contact between the formulation and the substrate (30 s), the crossbar was raised at a defined, constant speed until the two surfaces separated.

A 20 N load cell was used for the measurements [J. Y. Chang, Y-K. Oh, H. S. Kong, E. J. Kim et al., J. Control. Release 82 (2002) 39-50; S. Skulason, T. Kristmundsdottir, W. P. Holbrook, Bio-Gels Pharmaceuticals].

Five measurements were taken for each sample; the parameters considered were the maximum breaking load (ML) and the adhesion work (W).

The operating conditions used in the study are reported below.

| Apparatus | Lloyd LRX Tensiometer | |
|---|---|---|
| | Equipped with clamps for adhesion tests | |
| Test conditions | Crossbar speed | 0.1 mm/s |
| | Load cell | 20 N |
| | Contact time between substrate and gel | 30 s |
| | Contact surface | rabbit gastric mucosa/Polypropylene |

Results

The results are shown in Table 1.

TABLE 1

| | Rabbit gastric mucosa | | Polypropylene | |
|---|---|---|---|---|
| FORMULATION | ML (N) | W (Nmm) | ML (N) | W (Nmm) |
| EXAMPLE 1 | 0.088 ± 0.017 | 0.095 ± 0.030 | 0.101 ± 0.019 | 0.099 ± 0.014 |
| EXAMPLE 2 | 0.076 ± 0.012 | 0.069 ± 0.010 | | |
| EXAMPLE 3 | 0.179 ± 0.032 | 0.155 ± 0.032 | | |

Example 5 pH 4.0 Diffusion Test of Gels of Examples 1, 2 and 3

Diffusion medium: lactate buffer, pH 4.0

Diffusion volume: 50 mL

Temperature: 37±0.5° C.

Agitation speed: 50 rpm

Quantity of sample: 1.5 g

Release area: 4.5 cm$^2$

Release membrane: cellulose acetate 0.45 μm.

The test for release of the drug from the gel was performed using diffusion cells, with cellulose acetate membranes having a 4.5 cm$^2$ surface. The quantity of gel applied was 1.5 g. At given times, an automated system took predetermined sample aliquots, with immediate UV spectrophotometer reading at 254 nm.

Figure 1:
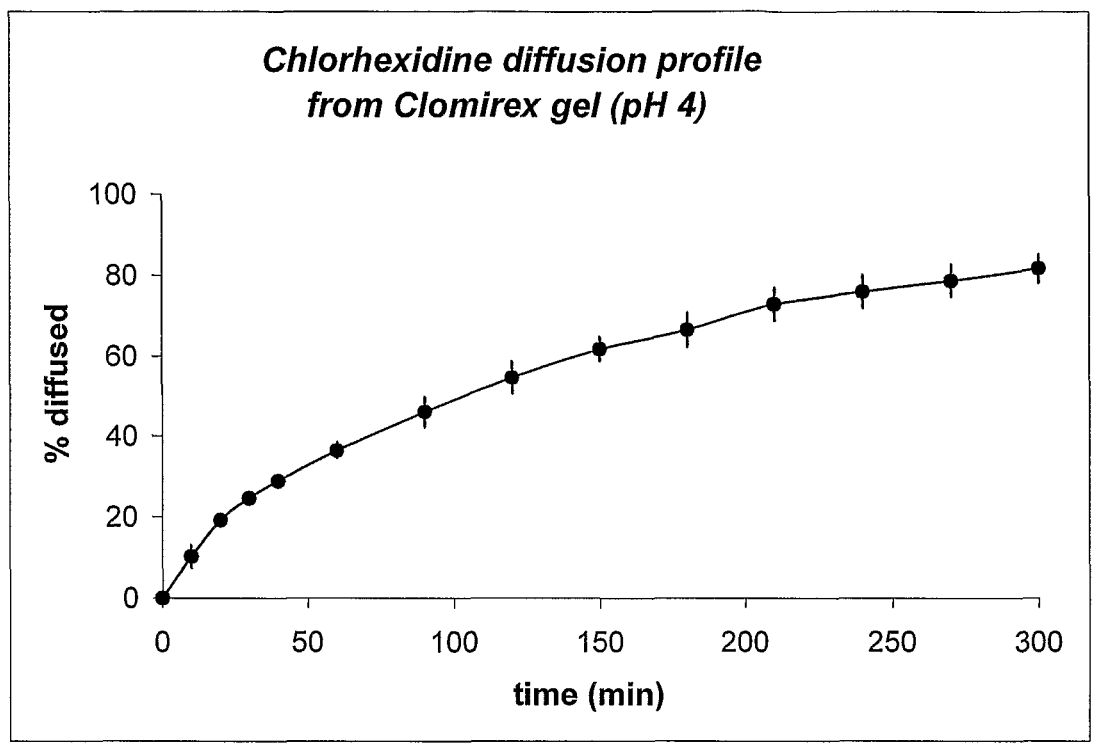
FIG. 1 shows the diffusion profile of chlorhexidine as the mean of 8 samples±standard deviation.
Figure 2:
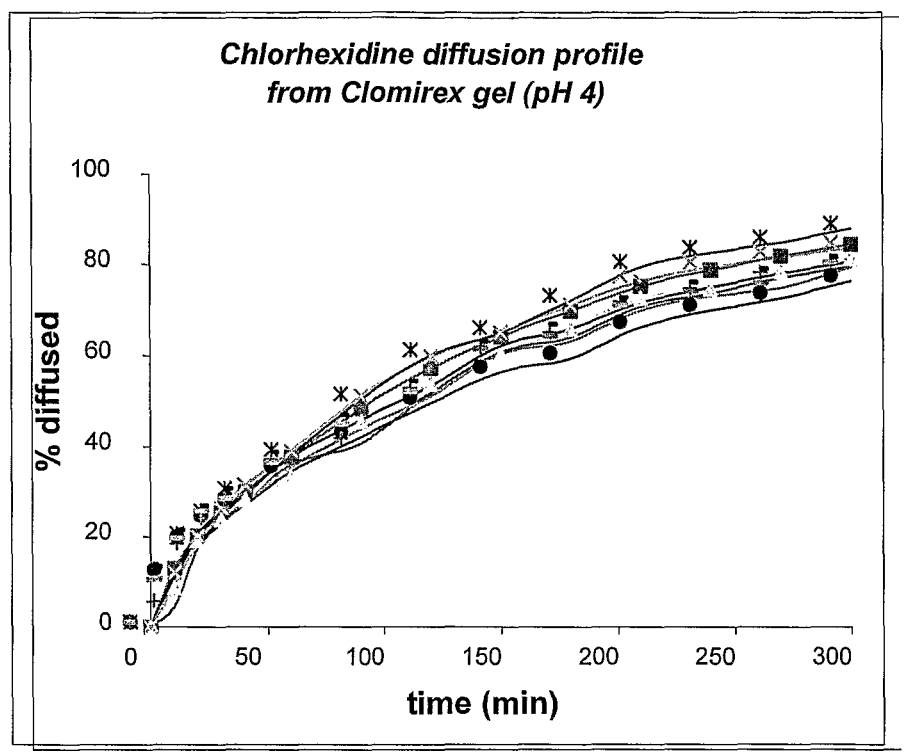
FIG. 2 shows the diffusion profile of chlorhexidine from the 8 samples.

Table 2 shows the percentages released for the 8 chlorhexidine samples.

TABLE 2

| time | sample 1 | sample 2 | sample 3 | sample 4 | sample 5 | sample 6 | sample 7 | sample 8 | mean | SD |
|---|---|---|---|---|---|---|---|---|---|---|
| 0 | 0 | 0 | 0 | 0 | 0 | 0 | 0 | 0 | 0 | 0 |
| 10 | 12.89 | 8.532 | 11.94 | 10.37 | 11.54 | 4.473 | 12.28 | 9.514 | 10.19 | 2.74 |
| 20 | 20.05 | 19.09 | 19.92 | 19.39 | 18.9 | 17.3 | 20.35 | 18.51 | 19.19 | 0.98 |
| 30 | 25.29 | 23.73 | 26.29 | 24.53 | 23.49 | 22.86 | 25.73 | 24.65 | 24.57 | 1.17 |
| 40 | 29.94 | 28.16 | 31.35 | 29.54 | 27.11 | 27.24 | 29.5 | 27.47 | 28.79 | 1.53 |
| 60 | 37.63 | 33.33 | 39.02 | 38.09 | 34.48 | 35.99 | 37.73 | 35.43 | 36.46 | 1.97 |
| 90 | 48.43 | 45.46 | 51.11 | 50.36 | 42.11 | 40.69 | 45.84 | 43.93 | 45.99 | 3.76 |
| 120 | 57.25 | 53.77 | 59.81 | 60.04 | 49.54 | 51.69 | 53.37 | 51.09 | 54.57 | 4.01 |
| 150 | 64.1 | 60.13 | 65.16 | 64.99 | 56.34 | 60.75 | 62.1 | 60.35 | 61.74 | 2.99 |
| 180 | 69.83 | 65.88 | 70.99 | 72.06 | 59.42 | 64.05 | 65.88 | 63.19 | 66.41 | 4.31 |

TABLE 2-continued

| time | sample 1 | sample 2 | sample 3 | sample 4 | sample 5 | sample 6 | sample 7 | sample 8 | mean | SD |
|---|---|---|---|---|---|---|---|---|---|---|
| 210 | 75.2 | 72.57 | 76.17 | 79.41 | 66.23 | 70.77 | 71.62 | 69.9 | 72.73 | 4.10 |
| 240 | 78.71 | 74.61 | 79.33 | 82.52 | 69.9 | 73.52 | 74.98 | 73.03 | 75.83 | 4.07 |
| 270 | 81.79 | 78.38 | 81.54 | 84.88 | 72.61 | 77.04 | 77.86 | 74.84 | 78.62 | 3.99 |
| 300 | 84.36 | 81.24 | 83.65 | 87.96 | 76.38 | 79.6 | 80.6 | 79.33 | 81.64 | 3.58 |

Figure 3:
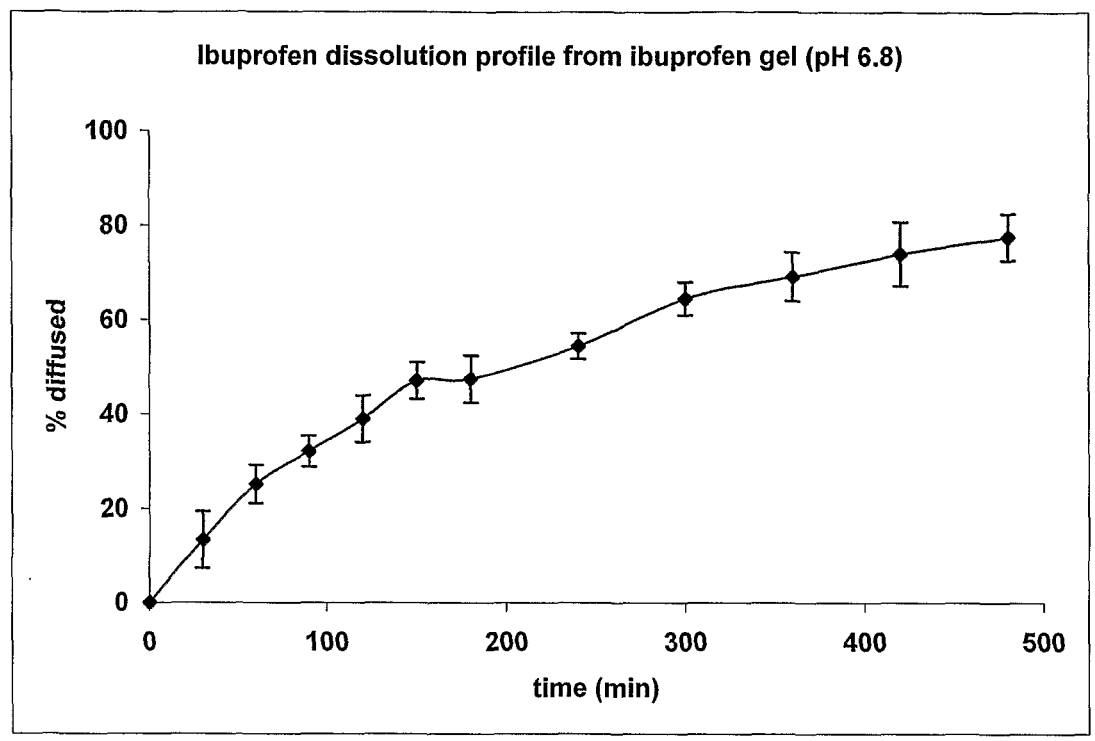

FIG. 3 shows the diffusion profile of ibuprofen as the mean of 8 samples±standard deviation.

Table 3 shows the percentages released for the 8 ibuprofen samples.

TABLE 3

| time (min) | sample 1 | sample 2 | sample 3 | sample 4 | sample 5 | sample 6 | sample 7 | sample 8 | mean | SD |
|---|---|---|---|---|---|---|---|---|---|---|
| 0 | 0 | 0 | 0 | 0 | 0 | 0 | 0 | 0 | 0 | 0 |
| 30 | 15.56 | 17.83 | 18.96 | 18.96 | 4.18 | 3.22 | 17.06 | 11.26 | 13.38 | 6.05 |
| 60 | 24.34 | 26.60 | 26.88 | 19.53 | 33.15 | 24.14 | 26.71 | 19.95 | 25.16 | 4.06 |
| 90 | 30.56 | 28.02 | 32.26 | 28.02 | 34.44 | 36.37 | 30.57 | 37.01 | 32.16 | 3.28 |
| 120 | 40.19 | 33.39 | 45.28 | 30.56 | 36.05 | 44.74 | 42.16 | 39.59 | 38.99 | 4.94 |
| 150 | 47.26 | 47.54 | 45.56 | 56.60 | 47.63 | 44.74 | 43.77 | 43.77 | 47.11 | 3.89 |
| 180 | 57.45 | 41.60 | 53.49 | 46.69 | 47.31 | 44.74 | 44.09 | 44.41 | 47.47 | 4.99 |
| 240 | 57.73 | 54.62 | 54.62 | 59.71 | 52.11 | 51.81 | 53.03 | 52.11 | 54.47 | 2.70 |
| 300 | 68.20 | 61.69 | 59.99 | 63.67 | 68.88 | 61.87 | 69.49 | 62.17 | 64.49 | 3.52 |
| 360 | 70.18 | 66.79 | 64.24 | 59.71 | 76.80 | 74.67 | 69.79 | 71.31 | 69.19 | 5.17 |
| 420 | 61.98 | 74.99 | 65.65 | 73.30 | 77.41 | 84.72 | 77.71 | 76.50 | 74.03 | 6.73 |
| 480 | 78.39 | 72.16 | 71.60 | 71.31 | 81.98 | 84.72 | 81.07 | 80.15 | 77.67 | 4.93 |

Figure 4:
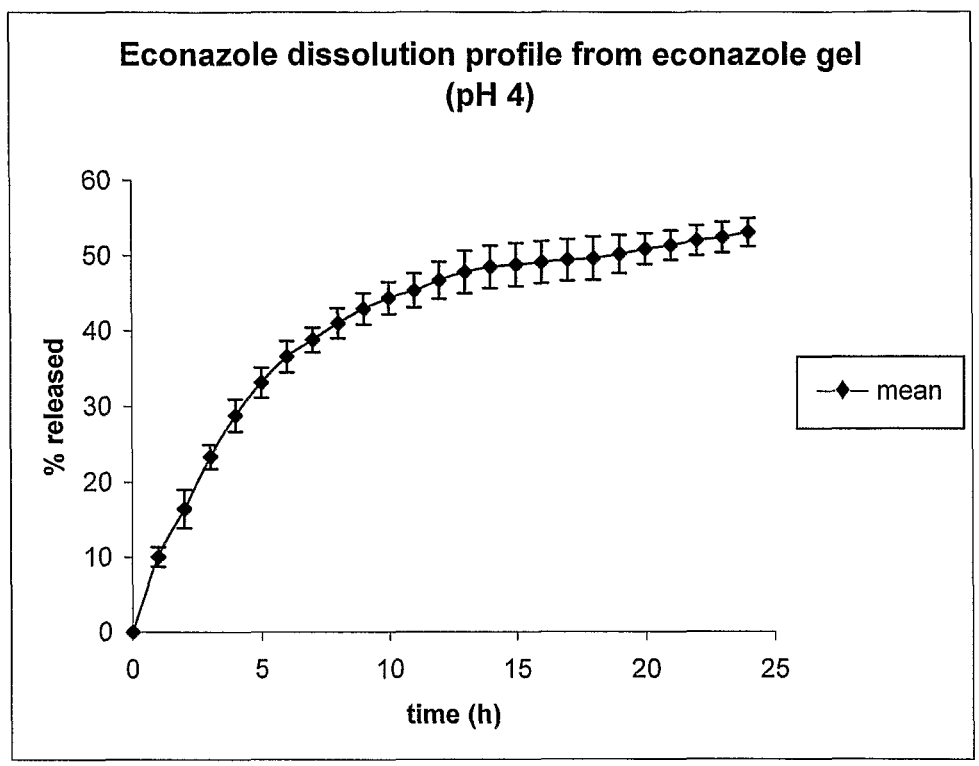

FIG. 4 shows the diffusion profile of econazole as the mean of 8 samples±standard deviation.

Table 4 shows the percentages released of the 8 econazole samples.

TABLE 4

| Time | sample 1 | sample 2 | sample 3 | sample 4 | sample 5 | sample 6 | sample 7 | sample 8 | mean | SD |
|---|---|---|---|---|---|---|---|---|---|---|
| 1 | 8.9 | 8.9 | 10.7 | 11.7 | 9.1 | 8.8 | 10.3 | 12 | 10.1 | 1.3 |
| 2 | 12.3 | 15.5 | 18.4 | 19.1 | 14.4 | 15 | 17.3 | 19.5 | 16.4 | 2.5 |
| 3 | 24.1 | 21.6 | 24 | 25 | 22.1 | 25.3 | 21.1 | 23.6 | 23.4 | 1.6 |
| 4 | 29 | 26.2 | 28.8 | 30.1 | 30.4 | 28.2 | 25.8 | 32.1 | 28.8 | 2.1 |
| 5 | 34.1 | 30.4 | 32.8 | 34.5 | 36 | 33.4 | 30.2 | 33.7 | 33.1 | 2.0 |
| 6 | 40 | 34.2 | 35.4 | 37.6 | 38.4 | 36.5 | 34 | 36.3 | 36.6 | 2.1 |
| 7 | 40.5 | 36.8 | 37.4 | 39.9 | 41 | 39.2 | 37 | 38.4 | 38.8 | 1.6 |
| 8 | 44.4 | 39.3 | 38.6 | 41.3 | 43.2 | 40.2 | 39.6 | 41.2 | 41.0 | 2.0 |
| 9 | 45.2 | 40.6 | 40 | 43 | 45.8 | 42.1 | 42.3 | 44.2 | 42.9 | 2.1 |
| 10 | 46.1 | 41.8 | 40.9 | 44 | 47.3 | 44 | 45 | 45.4 | 44.3 | 2.1 |
| 11 | 47.2 | 42.8 | 41.4 | 44.8 | 48 | 45.3 | 46.3 | 46.7 | 45.3 | 2.3 |
| 12 | 48.6 | 43.6 | 42.6 | 45.8 | 49.2 | 47.1 | 48.2 | 48.1 | 46.7 | 2.4 |
| 13 | 49.2 | 44.3 | 43.1 | 46.4 | 50.3 | 49.6 | 50.2 | 49.2 | 47.8 | 2.8 |
| 14 | 50.2 | 45.2 | 43.6 | 46.9 | 51 | 49.8 | 50.8 | 50.1 | 48.5 | 2.8 |
| 15 | 50.7 | 45.4 | 43.7 | 47.6 | 51.1 | 50 | 51.1 | 50.6 | 48.8 | 2.9 |
| 16 | 51.3 | 46 | 44.3 | 47.4 | 51.3 | 50.3 | 51.4 | 50.8 | 49.1 | 2.8 |
| 17 | 51.9 | 46.3 | 44.7 | 47.7 | 51.5 | 50.4 | 51.7 | 50.9 | 49.4 | 2.8 |
| 18 | 52.6 | 46.3 | 45 | 47.7 | 51.7 | 50.7 | 51.9 | 51.1 | 49.6 | 2.9 |
| 19 | 53.1 | 46.8 | 46.7 | 48.2 | 52 | 51.1 | 52 | 51.3 | 50.2 | 2.5 |
| 20 | 53.3 | 46.9 | 49.3 | 50.1 | 52.2 | 51.2 | 52.3 | 51.5 | 50.9 | 2.0 |
| 21 | 53.1 | 47 | 52.2 | 50.3 | 52.3 | 51.4 | 52.6 | 51.7 | 51.3 | 1.9 |
| 22 | 53.9 | 47.8 | 54.2 | 51.2 | 52.5 | 51.6 | 52.7 | 51.9 | 52.0 | 2.0 |
| 23 | 54.1 | 48.3 | 55.3 | 51.9 | 52.7 | 51.8 | 52.9 | 52.2 | 52.4 | 2.0 |
| 24 | 55.2 | 50.1 | 56.1 | 52 | 53.2 | 52.4 | 53.1 | 52.4 | 53.1 | 1.9 |

What is claimed is:

1. A method of delivering an active ingredient in the form of a bioadhesive gel composition to the mucosa of a subject in need thereof, said method comprising applying to an outer surface of said mucosa a composition consisting essentially of said active agent, glycerol and diethylene glycol monoethyl ether together with surfactants, preservatives and acidifiers, said composition formed into a gel and rendered bioadhesive by addition thereto of hydroxyethylcellulose.

2. The method according to claim 1, wherein said mucosa is a vaginal mucosa of said subject.

3. A method of delivering an active ingredient in the form of a bioadhesive gel composition to the mucosa of a subject in need thereof, said method comprising applying to an outer surface of said mucosa a composition consisting essentially of more than 2% and less than 4% by weight of hydroxyethylcellulose, 25 to 90% by weight of water, 5 to 25% by weight of glycerol, 5 to 50% by weight of diethylene glycol monoethylether, 0.01 to 10% by weight of surfactant, 0.05 to 1% by weight preservative an 0.01 to 1% by weight of acidifier.

4. The method according to claim 1, wherein said active ingredient consists essentially of one active agent selected from the group consisting of antifungals, antiseptics, local anaesthetics, antihistamines, anti-inflammatory agents, contraceptives, hormones and combinations thereof.

5. The method according to claim 4, wherein said active ingredient is selected from the group consisting of econazole, miconazole, fluconazole, cyclopiroxolamine, nifuratel, chlorhexidine, ibuprofen, ketoprofen, naptoxen, benzydamine, benzalkonium chloride or other quaternary ammonium antiseptics and nonxynol-9.

* * * * *